US008214029B2

(12) United States Patent
Koeneman et al.

(10) Patent No.: US 8,214,029 B2
(45) Date of Patent: Jul. 3, 2012

(54) SYSTEM AND METHOD FOR NEUROMUSCULAR REEDUCATION

(75) Inventors: Edward J. Koeneman, Tempe, AZ (US); James B. Koeneman, Tempe, AZ (US); Donald E. Herring, Tempe, AZ (US); Robert S. Schultz, Tempe, AZ (US)

(73) Assignee: Kinetic Muscles, Inc., Tempe, AZ (US)

( * ) Notice: Subject to any disclaimer, the term of this patent is extended or adjusted under 35 U.S.C. 154(b) by 123 days.

(21) Appl. No.: 12/758,706

(22) Filed: Apr. 12, 2010

(65) Prior Publication Data

US 2010/0198115 A1 Aug. 5, 2010

Related U.S. Application Data

(62) Division of application No. 10/727,212, filed on Dec. 2, 2003, now Pat. No. 7,725,175.

(60) Provisional application No. 60/430,700, filed on Dec. 4, 2002.

(51) Int. Cl.
*A61B 5/04* (2006.01)
*A61B 5/103* (2006.01)
*A61B 5/117* (2006.01)
*A61H 1/00* (2006.01)
*A61H 1/02* (2006.01)
*A61H 5/00* (2006.01)

(52) U.S. Cl. ......... 600/546; 600/587; 600/595; 601/23; 601/33

(58) Field of Classification Search ................. 600/587, 600/592, 595, 546; 601/23, 27, 33; 607/48, 607/49

See application file for complete search history.

(56) References Cited

U.S. PATENT DOCUMENTS

| 3,983,865 A | 10/1976 | Shepard |
| 4,582,049 A | 4/1986 | Yivisaker |
| 4,653,479 A | 3/1987 | Maurer |
| 4,683,891 A | 8/1987 | Cornellier et al. |
| 4,724,842 A | 2/1988 | Charter |
| 4,824,103 A | 4/1989 | Smidt |
| 5,012,820 A | 5/1991 | Meyer |
| 5,112,296 A | 5/1992 | Beard et al. |
| 5,330,516 A | 7/1994 | Nathan |
| 5,417,717 A | 5/1995 | Salo et al. |
| 5,466,213 A | 11/1995 | Hogan et al. |
| 5,549,656 A | 8/1996 | Reiss |
| 5,562,707 A | 10/1996 | Prochazka et al. |
| 5,674,262 A | 10/1997 | Tumey |
| 5,836,995 A | 11/1998 | MGraw et al. |

(Continued)

FOREIGN PATENT DOCUMENTS

GB 2227173 7/1990

(Continued)

OTHER PUBLICATIONS

International Search Report dated May 24, 2003.

*Primary Examiner* — Max Hindenburg
*Assistant Examiner* — Jonathan M Foreman
(74) *Attorney, Agent, or Firm* — Greenberg Traurig, LLP

(57) ABSTRACT

A system and a method that promotes the restoration of physical functions of the neuromuscular system by incorporating into one device the treatment modalities of biofeedback based repetitive practice, includes an actuator, a joint position measurement system, a force sensing measurement system, an EMG measurement system, a neuromuscular low-level stimulation system, a controller, and a display device.

19 Claims, 14 Drawing Sheets

U.S. PATENT DOCUMENTS

| | | |
|---|---|---|
| 5,860,941 A | 1/1999 | Saringer et al. |
| 5,951,499 A | 9/1999 | Saringer et al. |
| 6,006,129 A | 12/1999 | Watson |
| 6,010,468 A | 1/2000 | Grove et al. |
| 6,010,912 A | 1/2000 | Davies |
| RE36,690 E | 5/2000 | McGraw et al. |
| 6,064,912 A | 5/2000 | Kenney |
| 6,146,341 A | 11/2000 | Sato et al. |
| 6,155,993 A | 12/2000 | Scott |
| 6,254,525 B1 | 7/2001 | Reinhardt et al. |
| 6,282,445 B1 | 8/2001 | Reinhardt et al. |
| 6,456,885 B1 | 9/2002 | Shiba et al. |
| 7,396,337 B2 | 7/2008 | McBean et al. |
| 7,461,079 B2 | 12/2008 | Walker et al. |
| 2002/0143277 A1 | 10/2002 | Wood et al. |

FOREIGN PATENT DOCUMENTS

| | | |
|---|---|---|
| WO | WO9101683 | 2/1991 |
| WO | WO02/13673 | 2/2002 |

*FIG. 14*
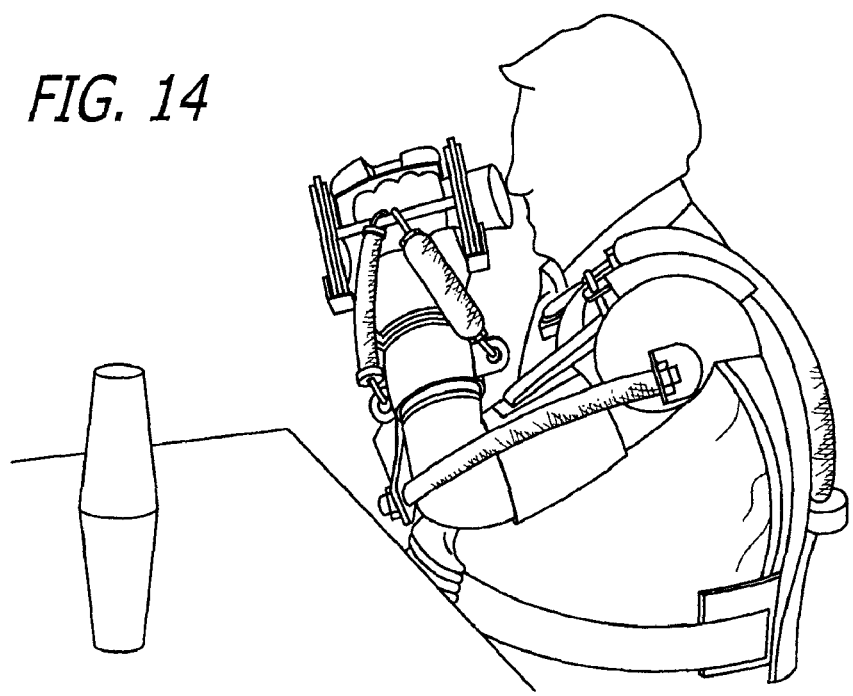
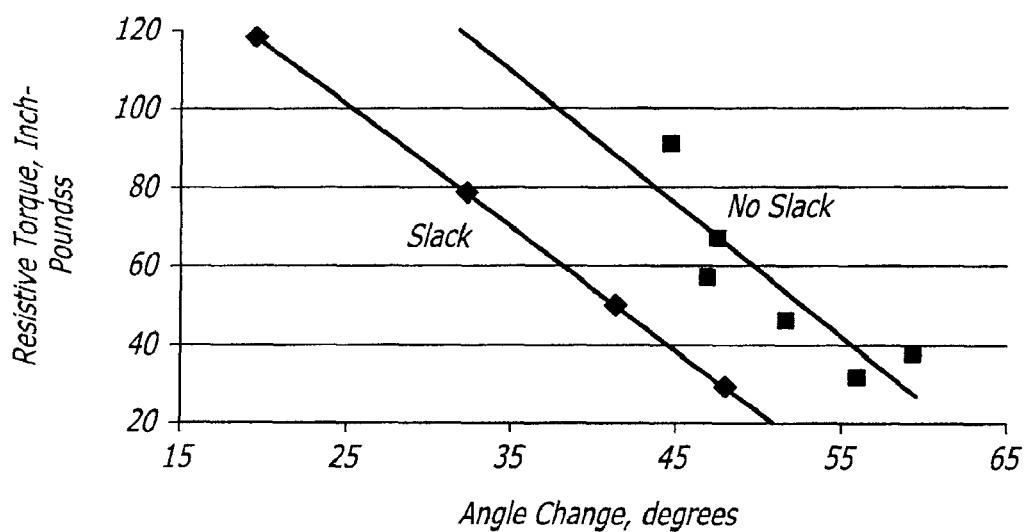
*FIG. 15*

SYSTEM AND METHOD FOR NEUROMUSCULAR REEDUCATION

RELATED APPLICATIONS

This application is a divisional of U.S. patent application Ser. No. 10/727,212, filed Dec. 2, 2003, which claims the benefit of U.S. Patent Application Ser. No. 60/430,700 filed Dec. 4, 2002, the contents of both of which are hereby incorporated by reference.

BACKGROUND OF THE INVENTION

1. Field of the Invention

The present invention broadly relates to bio monitoring in patients, and deals more particularly with a system and a method for implementing a protocol for restoring physical functions of the neuromuscular system through biofeedback.

2. General Background and State of the Art

Many people have movement disabilities caused by disease or injury. Among the causes are cerebrovascular accident or stroke (CVA), traumatic brain injury, multiple sclerosis, spinal cord injury and Parkinson's disease. Stroke is the leading cause of disability in the United States with at least 700,000 new cases each year. Over half of these people have residual physical disability. Current stroke therapy is labor-intensive and costly. Often insurance does not cover the cost of full therapy. One estimate is that the United States spends $30 billion per year to take care of stroke survivors. Seventeen billion dollars of this cost is direct medical expenditures and thirteen billion dollars represent an indirect cost due to lost productivity. Another estimate is that the total direct and indirect costs of stroke are $43.3 billion per year. The number of strokes is projected to increase because of the increase in the over 50 "baby boom" population. Also, new pharmaceutical treatments for stroke are projected to increase the number of patients surviving a stroke and increase the percentage of stroke survivors requiring rehabilitation. Therefore, it is not surprising that a recent estimate indicates the prevalence of stroke will more than double over the next 50 years.

Following a stroke, the initial treatment is to stabilize the patient. This usually occurs in an emergency room and critical care unit. Following stabilization, the patient is typically transferred to a hospital rehab unit. The time in a rehab unit has been significantly reduced in recent years by the pressures of health care reimbursement but could be as much 14 days. Because of the reduced time, very little therapy aimed at restoring function is applied. Patient activities involve learning toileting, transfers between locations and how to perform functions with the unaffected limb which reinforces learned non-use and hinders restoration of function of the affected limb. The level of disability and availability of health care funds determines where the patient goes following discharge from the rehab unit. The most severely afflicted go to a nursing home. Some patients receive comprehensive treatment in Day Treatment facilities, whereas some patients go to outpatient facilities for treatment of specific functional losses, while others receive home health treatment from visiting therapists.

Because of health care reimbursement reductions, therapy time for stroke patients has been significantly decreased. Currently, a majority of time spent in therapy post-stroke concentrates on helping a patient adapt to their disability by teaching toileting skills and transfers. A consequence of this treatment is the emergence of "learned nonuse" that hinders the restoration of available function. Most current rehabilitation therapies are administered on a spaced basis. Recently, concentrated therapies have been developed that improve function in CVA patients by reversing the effects of "learned nonuse". Animal studies suggest that learned nonuse is established immediately after the initial organic damage. A patient is punished for trying to use the affected limb and is rewarded for using other parts of the body. Over time, healing of the organic damage occurs but the suppression of use learned in the acute phase remains in force. Also, many of the therapies that have been shown to be effective in restoring function involve massed practice. Physical Therapy training techniques have been used by researchers. Significant improvement in limb function was obtained in chronic CVA patients.

Training techniques based on electromyographic (EMG) biofeedback improve motor ability of chronic CVA patients, as demonstrated by some studies. Repetitive concentrated practice produced large therapeutic effects for lower limb function. Researchers have also systematically studied a variation of forced use of hemiplegic extremities which has been labeled Constraint-Induced (CI) Movement Therapy. Some of these experiments compared several massed therapy techniques and all showed very large increases in limb use over the treatment period.

Two very sophisticated robot systems are being developed for treatment and evaluation of CVA patients which have shown some effectiveness in treatment of CVA patients and have developed very useful data for understanding recovery mechanisms; however, the current cost of these systems precludes their widespread clinical use.

Other studies have shown that measured EMG can be used to trigger neuromuscular electrical stimulation in restoring function to CVA patients. However, the discomfort of surface neuromuscular stimulation significantly limits the clinical implementation of this modality for persons with hemiplegia. EMG biofeedback treatment of stroke patients has also shown some success. This treatment uses surface electrodes to capture the electrical activity of a selected muscle group. An electronic unit converts the signals into visual or audio information for the patient. This information is used by the patient to augment or decrease muscle activity.

Accordingly, what are needed are a system and a method that promotes the restoration of physical functions of the neuromuscular system by incorporating into one device, the treatment modalities of repetitive practice, and force and EMG biofeedback. Furthermore, the system should be inexpensive, portable, comfortable, and easy to use either by the patient or by a therapist.

INVENTION SUMMARY

The system according to the present invention will assist in therapy by supplying increased amounts of information to the physician/therapist while reducing the amount of patient contact time. The system is adaptable to accommodate the changing paradigm of cerebrovascular accident (CVA) rehabilitation service delivery and to assist in studies designed to refine therapy protocols.

Accordingly, in one aspect of the invention, the system for neuromuscular function reeducation and restoring physical function of a neuromuscular system, associated with a joint in a patient, includes at least one sensor for measuring an electrical signal associated with an agonist muscle in the neuromuscular system of the patient. The electrical signal associated with the agonist muscle is used to provide visual feedback for controlling the joint extension and flexion thereby enabling reeducation and restoration of the physical function of the neuromuscular system.

In another aspect of the invention, the system for neuromuscular function reeducation and restoring physical function of a neuromuscular system, associated with a joint in a patient, includes at least one sensor for measuring an electrical signal associated with an agonist muscle in the neuromuscular system of the patient, at least one sensor for measuring an electrical signal associated with an antagonist resisting muscle. The electrical signal associated with the agonist muscle and the electrical signal associated with the antagonist resisting muscle are combined to form a net signal which is used to provide visual feedback for controlling the joint extension and flexion thereby enabling reeducation and restoration of the physical function of the neuromuscular system.

In another aspect of the invention, the system for neuromuscular function reeducation and restoring physical function of a neuromuscular system, associated with a joint in a patient, includes at least one sensor for measuring an electrical signal associated with an agonist muscle in the neuromuscular system of the patient, at least one sensor for measuring an electrical signal associated with an antagonist resisting muscle, at least one electrode for providing a low-level neuromuscular stimulation to the neuromuscular system. The electrical signal associated with the agonist muscle and the electrical signal associated with the antagonist resisting muscle can be viewed separately or combined to form a net signal which is used to provide visual feedback, the visual feedback and the low-level neuromuscular stimulation being used for controlling the joint extension and flexion thereby enabling reeducation and restoration of the physical function of the at least one neuromuscular system.

In another aspect of the invention, the system for neuromuscular function reeducation and restoring physical function of a neuromuscular system, associated with a joint in a patient, includes at least one continuous passive device for allowing the extension and flexion of the joint, wherein the continuous passive device permitting self-actuation of the neuromuscular system, at least one force sensor for measuring a parameter indicative of resistance of an antagonist resisting muscle, the antagonist resisting muscle associated with the neuromuscular system. The parameter which indicates the resistance of the antagonist resisting muscle is used for controlling the joint extension and flexion thereby enabling reeducation and restoration of the physical function of the at least one neuromuscular system.

In another aspect of the invention, the system for neuromuscular function reeducation and restoring physical function of at least one neuromuscular system, associated with an at least one joint in a patient, includes: (i) a motion causing device adjacent to the joint, the motion causing device permitting self-actuation of the neuromuscular system; (ii) at least one force sensor for measuring a parameter indicative of the muscle resistance; (iii) at least one joint position sensor for measuring joint movement; (iv) at least one neuromuscular electrical stimulating (NMES) system; (v) an electronic memory system that stores information of the patient; (vi) at least one EMG sensor for measuring the electrical activity of the neuromuscular system; and (vii) a controller that implements a protocol for controlling the joint motion based on the measurements from the sensors thereby restoring physical function of the neuromuscular system associated with the joint.

In one embodiment of the present invention, the motion-causing device could be an inflatable device, such as a pneumatic air-muscle, having two ends, wherein one end is connected to a distal element of the joint and the other end to a proximal element of the joint. Such a device has the property that increasing the diameter, by supplying pressurized air for it to inflate, causes it to shorten thereby causing the joint to pivot about at least one axis. Like human muscle, this device has spring-like characteristics, is flexible, and is lightweight. Moreover, the force-deflection characteristics can be made substantially similar to those of human muscle.

In conjunction with the system for neuromuscular function reeducation and restoring physical function of at least one neuromuscular system, the present invention includes a method for implementing a protocol for restoring physical function of the neuromuscular system associated with an at least one joint in a patient. This method comprises: (i) measuring a first signal indicative of the activity of a muscle, in the neuromuscular system, through an EMG sensor; (ii) measuring a second signal indicative of the joint motion through a joint position sensor; (iii) measuring a third signal indicative of the muscle resistance through a force sensor; (iv) mapping the measured signals to at least one parameter; and (v) controlling the air level in an inflatable device (such as the pneumatic air-muscle) in order to optimize the parameter for restoring physical function of the muscle, in the neuromuscular system, associated with the joint in the patient.

Furthermore, although repetitive task practice therapies have been shown to be effective, a significant number of stroke survivors have insufficient hand motion to participate fully in these activities. Studies have shown that the Tonic Vibration Reflex (TVR) lowers recruitment thresholds of agonist muscle groups and inhibit activation of antagonistic muscle groups. This tonic reflex mechanism of the agonist muscle is stimulated by prolonged vibration of its tendon. These trains of vibration to a tendon of a receptor-bearing muscle stimulate human spindle primary afferents which cause autogenetic muscle contraction. For example, TVR activation of wrist and finger muscles can be used to enhance the motion and functionality of stroke patients that have high flexor muscle tone and low extensor motion. Thus, another aspect of the invention incorporates a vibrator to stimulate the TVR.

Thus, in another aspect of the invention, the system for neuromuscular function reeducation and restoring physical function of a neuromuscular system, associated with a joint in a patient, includes at least one sensor for measuring an electrical signal associated with an agonist muscle in the neuromuscular system of the patient, at least one sensor for measuring an electrical signal associated with an antagonist resisting muscle, at least one vibrator to excite the TVR. The electrical signal associated with the agonist muscle and the electrical signal associated with the antagonist resisting muscle can be viewed separately or combined to form a net signal which is used to provide visual feedback, the visual feedback and the low-level neuromuscular stimulation being used for controlling the joint extension and flexion thereby enabling reeducation and restoration of the physical function of the at least one neuromuscular system.

The above and other objects, features, and advantages of the present invention will become apparent from the following description read in conjunction with the accompanying drawings.

BRIEF DESCRIPTION OF THE DRAWINGS

FIG. 14 is a final state of the air-muscle device used in conjunction with a robotic system for providing assistive training; and FIG. 15 is an exemplary plot depicting the torque calibration curves for two strap conditions.

DETAILED DESCRIPTION OF THE PREFERRED EMBODIMENTS

Figure 1:
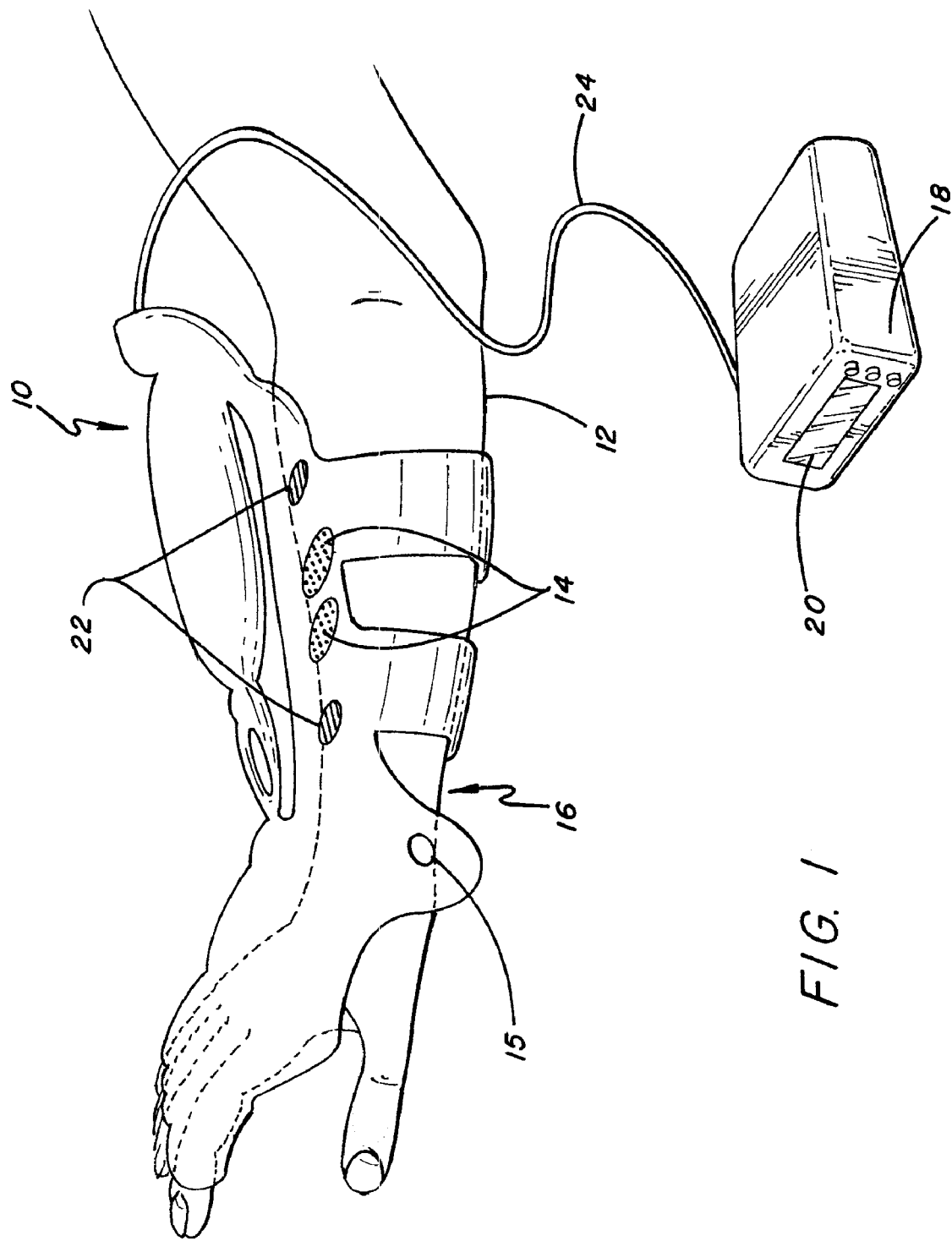
FIG. 1 shows one embodiment of the motion causing device, which is the air-muscle described herein, attached to the proximal forearm along with various sensors and a controller box.

Referring now to the drawings and in particular to FIG. 1, there is shown motion causing device or an actuator 10 attached to the proximal forearm 12 along with various sensors 14, 15 for monitoring activity along the proximal forearm 12 and the at least one joint 16, at least one electrostim electrode 22 for providing a low-level neuromuscular stimulation, and a controller box 18 with a display port 20 for providing visual feedback for a patient/therapist. The system shown in FIG. 1 is used for neuromuscular function reeducation and restoring physical function of at least one neuromuscular system.

It is important that the actuator 10 permit relative motion between the proximal and distal portions of the joint 16 in a manner to minimize any hindrance or interference with any motion generated by the patient's neuromuscular system.

In one embodiment, the actuator 10 is a pneumatically operated air-muscle. A prior art artificial muscle device exhibits many of the properties of human muscle. The artificial muscle device consists of an expandable internal bladder (e.g., a rubber tube) surrounded by a braided shell. When the internal bladder is pressurized, it expands radially against the braided shell causing the muscle to contract. Braided finger traps used to hold fingers on traction devices contract radially when pulled. The air-muscle, according to one embodiment in the present invention, works in the same manner but in the opposite direction (i.e., increasing the diameter causes it to shorten). Like human muscle, the device has spring-like characteristics, is flexible, and is lightweight. The force-deflection characteristics can be made similar to those of human muscle. Pressurized air canisters or accumulators that are recharged by air compressors can be used as a source for supplying air to the air-muscle. Major advantages of the air muscle are its flexibility and ease of adaptation to address the specific loss of function exhibited by a patient. Additionally, the device of the preferred embodiment has three times the pull force of an air piston of the same cross sectional area. The utility of this device resides in its unique combination of attributes: low cost, lightweight, low profile, and low noise operation.

Figure 5A:
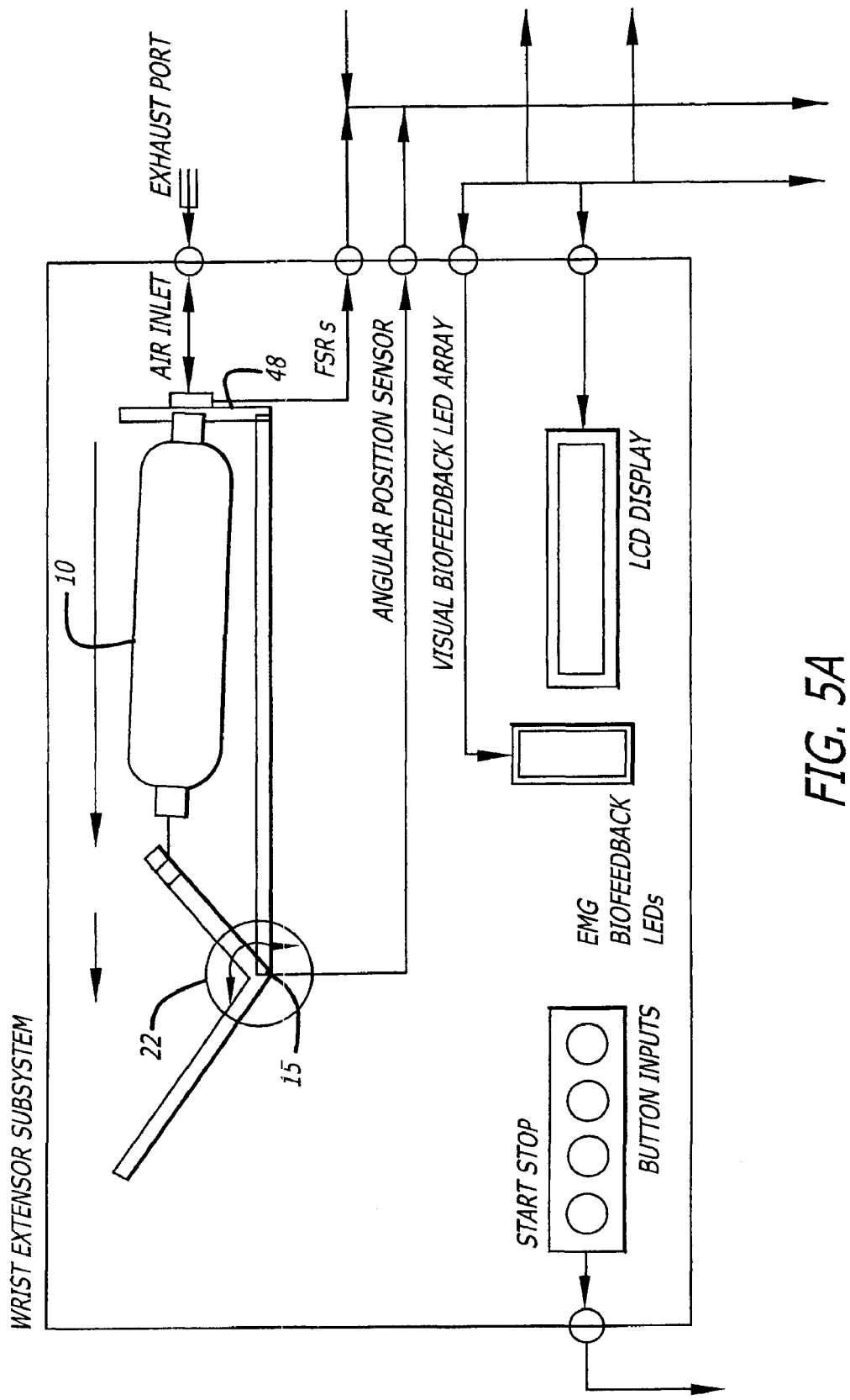
FIG. 5 is a block diagram showing one embodiment of the present system for neuromuscular function reeducation and restoring physical function of at least one neuromuscular system.

The sensors include at least one joint position sensor 15 for measuring joint movement, at least one force sensor 48 (shown in FIG. 5A) for measuring a parameter indicative of the muscle resistance, at least one EMG sensor 14 for measuring the electrical activity of the neuromuscular system. Furthermore, there is at least one neuromuscular electrical stimulating (NMES) device, such as an electrostim electrode 22, for providing low-level neuromuscular stimulation.

The controller box 18, connected through cable 24 to the air-muscle 10, includes electronics (i) for recording and displaying 20 measurements obtained through various sensors 14, 15, and (ii) for controlling the air-muscle 10 operation (e.g., by controlling the supply of air into the muscle). This controller box 18 is a self-contained, mobile device that provides sensory (e.g., visual) feedback of wrist and finger position, EMG extensor activity and wrist flexor resistive torque. Alternatively, the sensory feedback could be provided through tactile sensing through piezoelectric transducer induced vibrations on the skin, or through audio signals (e.g., beeps through an auditory display). The firmware in the microprocessor of the controller system 18 has been designed to be well-structured using object-oriented programming techniques. Use of these techniques yields more reliable code having fewer discrepancies and problems. The controller box 18 is shown as a separate device, however it is to be understood that the box could be a sleeve wrapped around the arm of a patient and as shown in FIG. 2.

Figure 2:
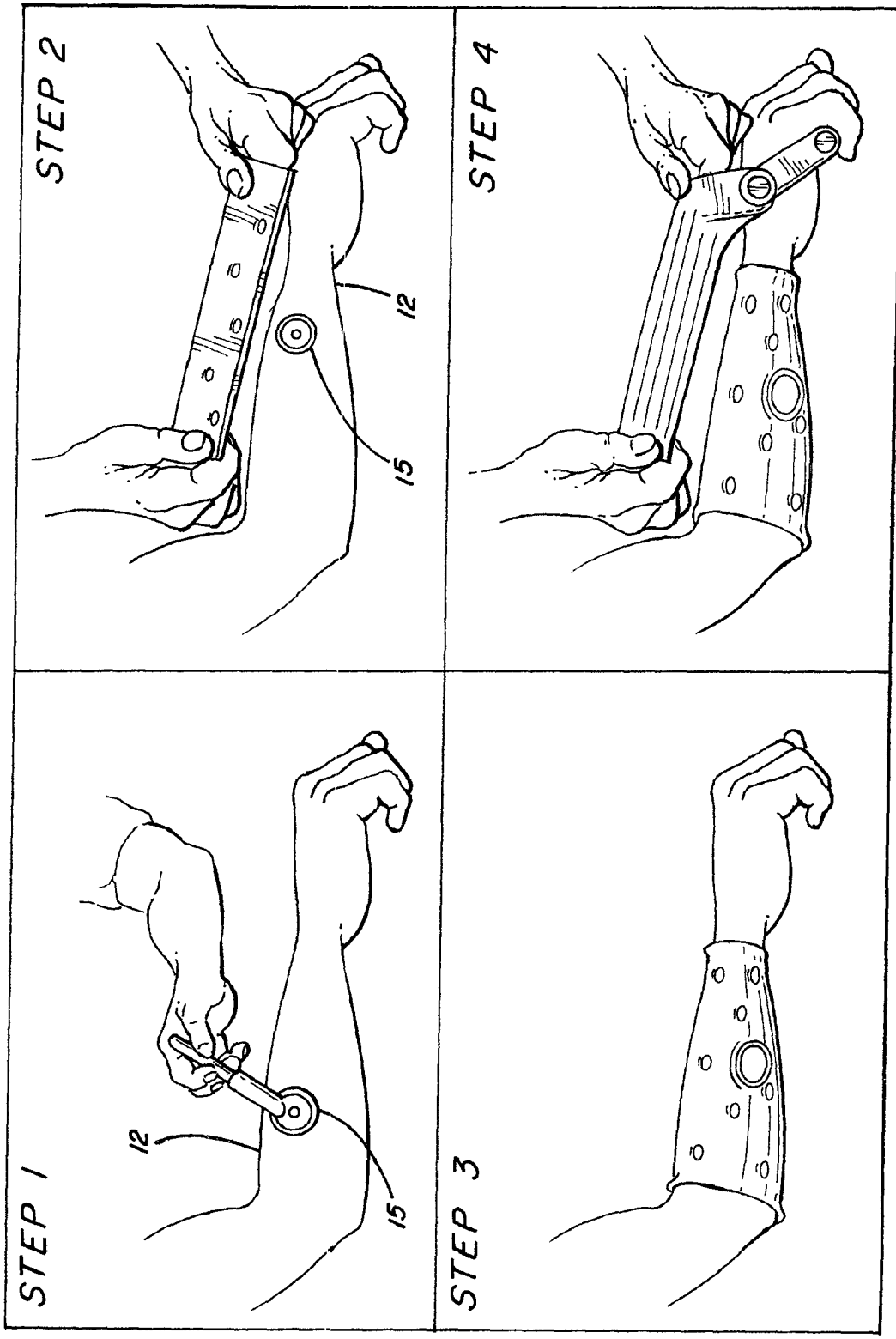
FIG. 2 depicts an exemplary procedure for attaching EMG electrodes for measuring joint extensor activity.

FIG. 2 depicts an exemplary procedure for attaching at least one EMG electrode 15 for measuring joint extensor activity (also known as the agonist muscle activity). Closely spaced surface electrodes are used to measure joint extensor EMG activity. The location of the EMG electrodes 15 is determined for each patient by the therapist. The skin may be rubbed several times with alcohol soaked gauze pads. The EMG electrode output is used to measure the relative recruitment of selected extensor muscles and may be used to feedback the information to the patient to reinforce correct recruitment. Session to session variation in EMG values may be recorded for monitoring patient performance and/or compliance. The EMG sensor may be used for measuring the electrical activity of an agonist muscle (e.g., the extensor muscle) and/or an antagonist resisting muscle (e.g., the flexor muscle) in the neuromuscular system of a patient. Two measuring channels may be used to capture EMG activity of the muscle sets of the neuromuscular system.

Figure 5B:
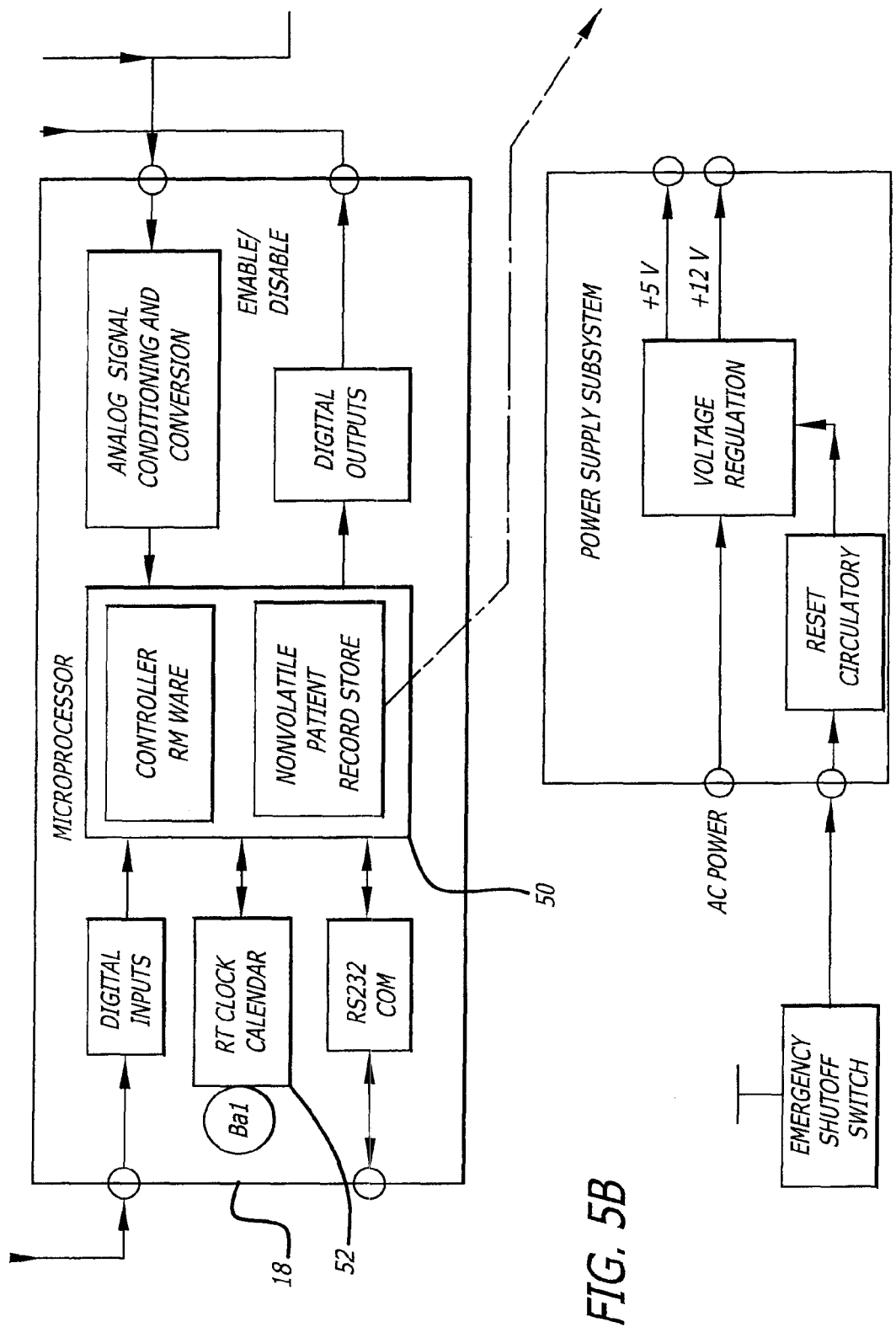
Figure 5C:
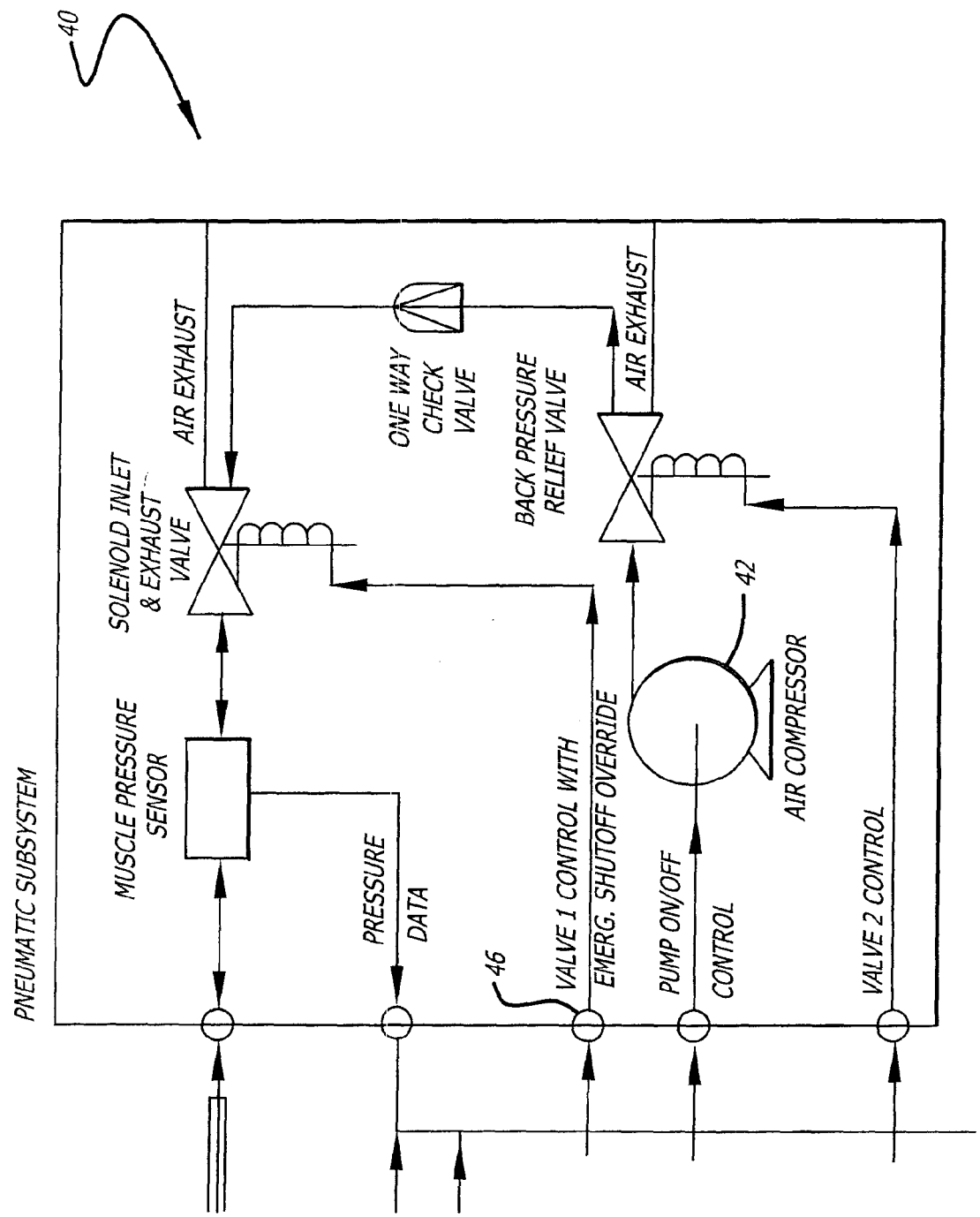
Figure 5D:
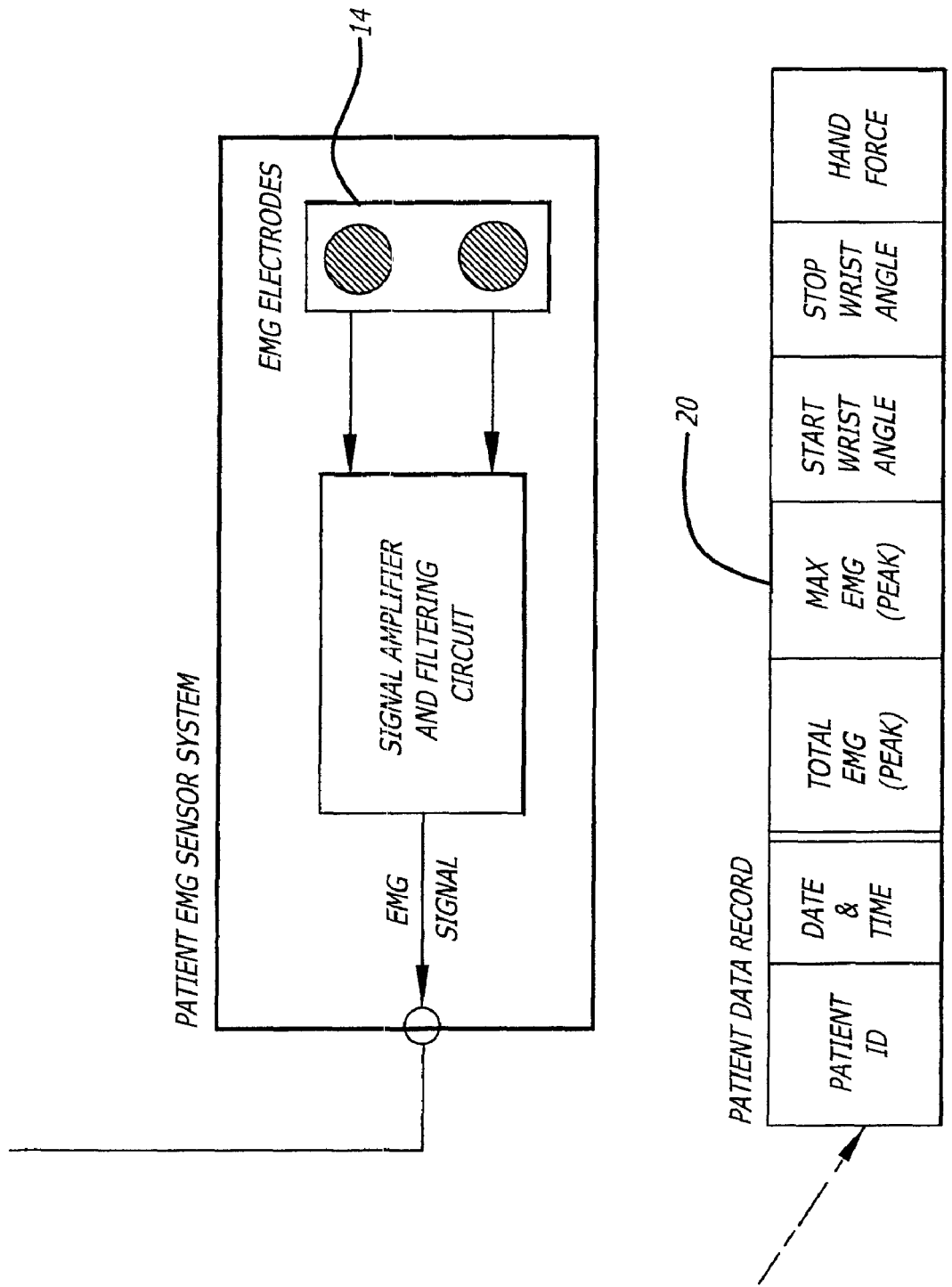

The air-muscle is supplied by compressed air by means of a source (FIG. 5, 42), and the air supply may be controlled by the controller 18 that includes a microprocessor (FIG. 5B) for controlling at least one valve (FIG. 5C, 46) that controls the supply of pressurized air to the air-muscle.

Figure 3:
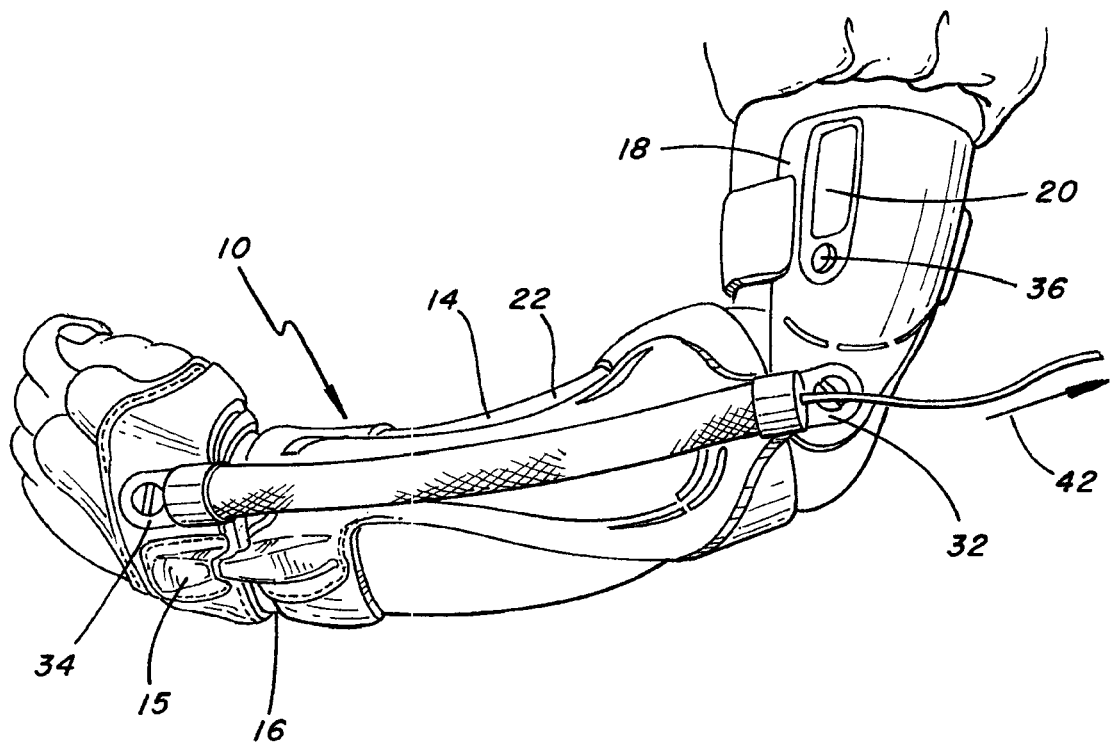
FIG. 3 shows one embodiment of the motion causing device, which is the air-muscle described herein, in at least two operational modes, namely the deflated mode and the inflated mode which flexes and extends, respectively, the wrist joint.
Figure 3:
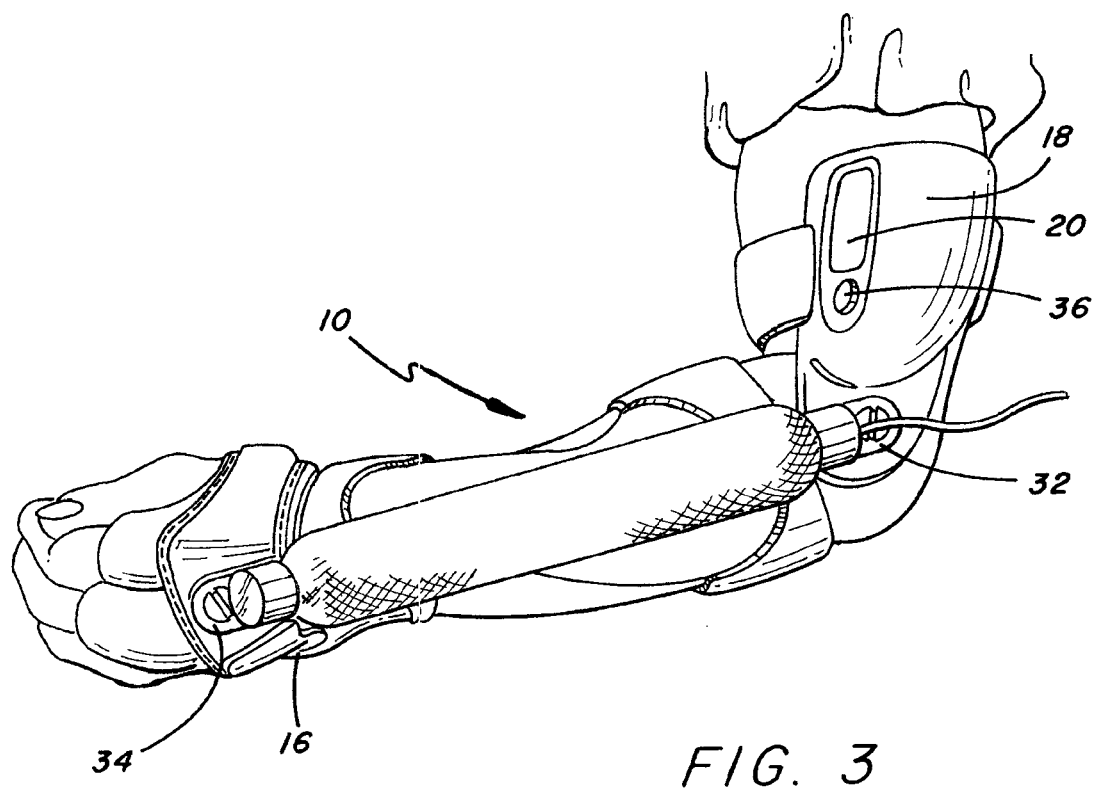
Figure 4:
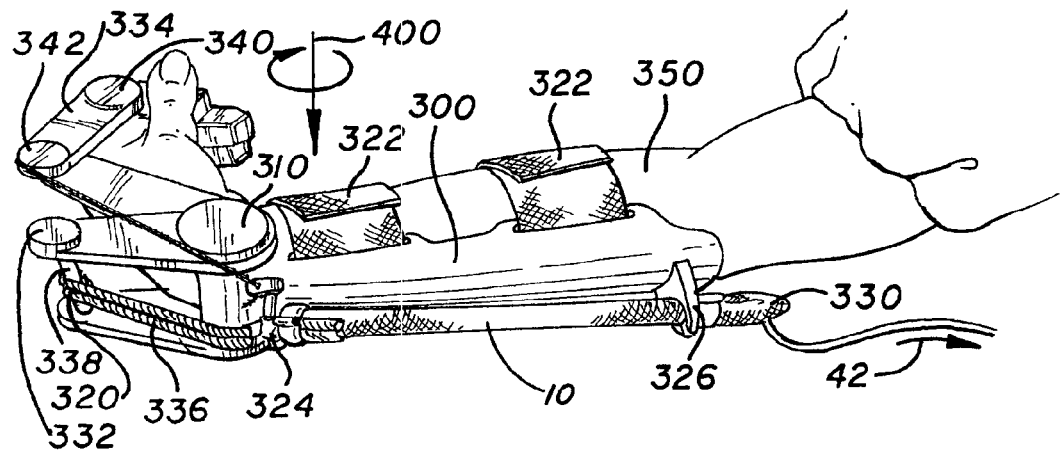
FIG. 4 shows another embodiment of the motion causing device, which is the air-muscle described herein permitting the wrist joint to be in flexion, neutral, and extended position respectively.
Figure 4:
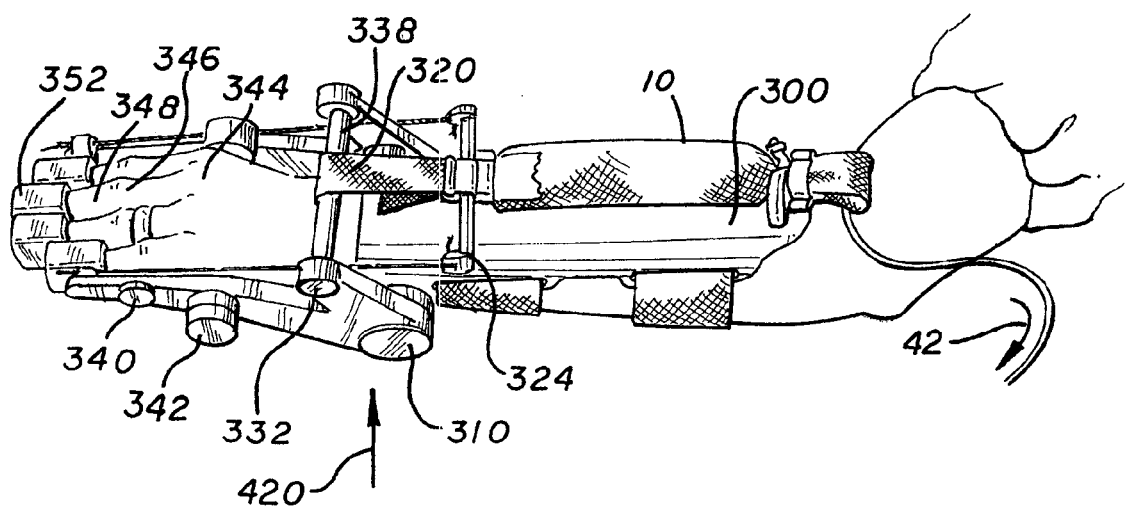
Figure 4:
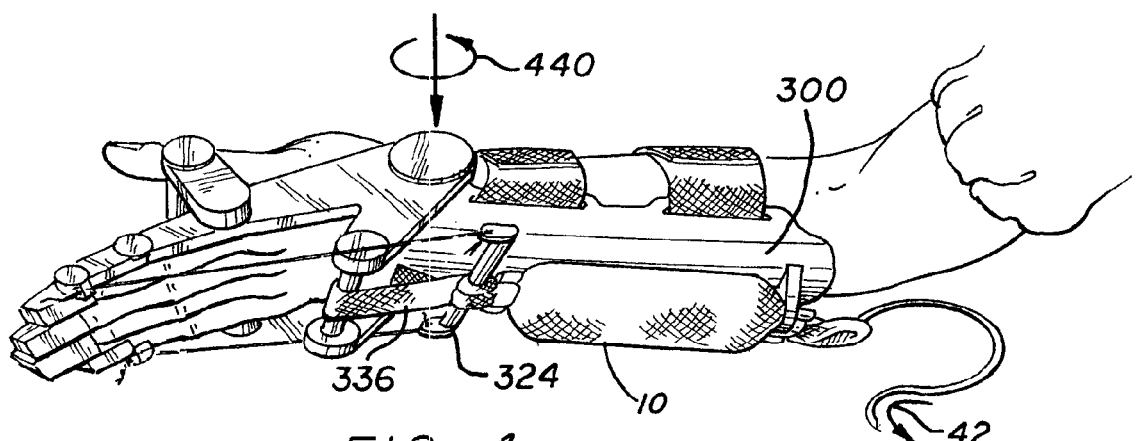

In one embodiment of the present invention, as shown in FIG. 3, one end of the air-muscle 10 is connected to a distal element 34 of the wrist joint 16 and the other end of the air-muscle 10 is connected to a proximal element 32 of the wrist joint 16. Activation of the air muscle 10, by inflating it through a supply source 42 (FIG. 5C) of air, may cause the joint to pivot about at least one axis and causing the joint to go from a flexed position to the extended position as shown in FIG. 3. As an example, this could be achieved by means of rotation of a bar that extends the wrist and operates a mechanism that extends the fingers and wrist between flexed, neutral, and extended positions as shown in FIG. 4. An optional data port 36 may be provided for downloading stored information from the memory 50 (FIG. 5) of controller 18 to a PC (not shown).

Now referring to FIG. 4, an alternative embodiment of the present invention is shown therein. Specifically, the wrist joint is shown in three states (flexion, straight, and extended). The air-muscle device 10 (shown with a braided type covering), having strap 330 for permitting air from a source 42, is connected at one end to the forearm support structure 300 via connector 326. The support 300 wraps around the forearm and is held in place by means of straps 322. The other end of the air-muscle 10 is connected to a bar 324 which also provides a pulley for the extension strip 336. One end 320 of the strip 336 is connected to a bar 338 with a corresponding joint 332. The other end of strap 336 is attached to the support structure 300. The joints, 342 and 340, of the support structure 300 are positioned adjacent the knuckles 344 and the finger joints 346, respectively, of the patient's hand. The structure 300 may also include tubes 352 for allowing the finger ends to be housed.

With regards to the operation of the device in FIG. 4, shown therein are three states that the wrist joint may achieve: (i) flexion, (ii) normal, and (iii) extension. Clearly, the device permits a very high number of states intermediate to the states shown in FIG. 4. The air-muscle 10 extends, relatively, in length, upon deflation (as shown in the top figure of FIG. 4), which causes the bar 338 to rotate/pivot clockwise (looking from the top and as depicted by the arrow 400) about joint 310. This causal effect is established by means of the strip 336 that connects the bar 338 to the air-muscle 10. This pivot action of the bar 338 causes the wrist to achieve the flexion state. Furthermore, rotation of the joints 342 and 340 may allow the knuckle joints and the finger joints to assume curled/retracted positions.

The air-muscle 10 shortens, relatively, in length, upon reasonable inflation (as shown in the middle figure of FIG. 4), which causes the bar 338 to rotate/pivot counter-clockwise (looking from the side and as depicted by arrow 420) about joint 310. This causal effect is established by means of the strip 336 that connects the bar 338 to the air-muscle 10. This pivot action of the bar 338 causes the wrist to achieve the normal or straight state. Furthermore, rotation of the joints 342 and 340 may allow the knuckle joints and the finger joints to assume substantially straightened positions.

The air-muscle 10 shortens, relatively, much more in length, upon a higher degree of inflation (as shown in the bottom figure of FIG. 4), which causes the bar 338 to further rotate/pivot counter-clockwise (looking from the top and as depicted by the arrow 440) about joint 310. This causal effect is established by means of the strip 336 that connects the bar 338 to the air-muscle 10. This pivot action of the bar 338 causes the wrist to achieve the extension state. Furthermore, rotation of the joints 342 and 340 may allow the knuckle joints and the finger joints to assume substantially extended positions.

Joint extension position or displacement is measured by the at least one joint position sensor 15, such as a potentiometer, that is incorporated in the motion causing device. Resistance to extension, that may be due to the antagonist resisting muscle, is measured by the at least one force sensor 48 (FIG. 5A), such as a force sensitive resistors (FSRs), that is placed on the device. The FSR output is a measure of the resistance of finger and wrist flexor muscles. Alternatively, the resistance to extension may be measured by at least one EMG sensor. Alternatively, the resistance to extension may be determined by measuring the maximum extension of a patient's hand under a specified activation pressure. The compliant property of the air muscle allows the lack of full extension to be calibrated versus the resisting load or torque.

If force sensors are used, the at least one force sensor 48 (i.e., the FSR) is calibrated after each device is assembled. A load cell (not shown) is inserted between an activation bar on the device and muscle. The mechanism is fixed in six different degrees of flexion-extension. The output of the FSR may be compared to the load cell output. The torque about the joint at each wrist position is calculated by multiplying the muscle force by the distance to the line of action of the air muscle.

As mentioned above in paragraph 44, the force sensing aspect may be simplified by simply measuring the performance of the air muscle. Specifically, when the air muscle is pressurized, external loads cause it to extend. Thus, the amount of extension caused by the resistance of spastic resisting muscles may be sufficiently large to be measured with the joint position potentiometer. The calibration of the amount of lengthening of the muscle may be achieved by determining the change in joint position potentiometer reading versus the resistive load. This calibration result may then be stored in the microprocessor. When the hand is extended by a prescribed pressure, the amount by which the extension motion is reduced from full extension is a measure of the resisting torque.

In another aspect of the invention, protection against overloading a limb is provided by the compliant nature of the pneumatic muscle. Because of this compliance, it may not to be necessary to provide an auxiliary exhaust if excessive resistance is encountered. The compliance also provides a method of measuring the resistive load, as confirmed through Mentor testing by means of a load cell inserted between the air muscle and the actuating bar of the hand mechanism. A data acquisition system recorded the load and the position as measured by the pivot potentiometer at 100 Hz. Resistive forces were generated by hanging weights on the hand piece and also by wearing the Mentor and manually resisting the motion with different levels of force. The resistive load versus the amount of extension is shown in FIG. 15. After one set of resistive measurements was made, the initial tightness of the strap connecting the bar to the load cell and the muscle was adjusted. The load versus amount of extension is linear but is a function of the adjustment of the strap. Based on these results, the force sensing was changed from force sensitive resistors (FSRs) to measuring the decrement from full extension. The load-rotation calibration of each Mentor is determined at the completion of assembly. These measurements also determine the rate of extension.

The motion causing device 10 (i.e., the air-muscle) drives the fingers and wrist into extension by moving a mechanical linkage. The linkage is designed to move the fingers and/or wrist in a spiral fashion. A therapist can also program the air-muscle(s) so that a desired motion pattern is followed for fastest and effective recovery.

Additionally, excessive force on the hand is prevented in several ways. A micro-compressor was chosen that has a maximum output pressure which limits the maximum force supplied by the air muscle. The air muscle is a very compliant drive with the maximum force output at the fully flexed position where the stretch reflex resistance of the flexor muscles is minimum. As extension proceeds, the stretch reflex increases resistance to motion. If a large resistance is encountered during extension, the air muscle stretches and limits the range of motion. Since spastic flexor muscles are velocity sensitive, the velocity of actuation was chosen to be about 5 degrees per second with no loading. With the weight of a flaccid hand this rate decreases to about 3.8 degrees per second and with mild resistance the rate is approximately 2.7 degrees per second. Previous experiments have shown only small increases in muscle tone occurring for very spastic hemiplegics due to velocity at rates below about 6 degrees per second. The rate in the present device is physically controlled by the volume capacity of the micro-compressor and the resistance in the pneumatic circuits. To prevent excessive extension of the wrist, a physical stop may be provided that limits motion of the activation bar at about 60 degrees of wrist extension. A safety panic switch that releases the air pressure is also provided on a tether and is placed close to the patient's side.

An important aspect for choosing the actuator to be an air-muscle is that the air-muscle permits relative motion between the proximal and distal portions of the joint, due to its high mechanical compliance, in a manner that does not hinder or interfere with any motion generated by the neuromuscular system. Allowing self-actuated motion of the joint by means of the neuromuscular system is an important element in the design. Specifically, the air-muscle allows unfettered self-actuated motion of the joint.

In another aspect of the invention, a continuous passive device, with a high mechanical compliance, that permits extension and flexion of the joint through self-actuation could be used for neuromuscular function reeducation and restoring physical function of the neuromuscular system.

FIG. 5 is a block diagram showing one embodiment of the present system for neuromuscular function reeducation and restoring physical function of at least one neuromuscular system showing the controller 18 with a microprocessor 44 and an electronic memory 50, the air-muscle 10, at least one display 20, at least one joint position sensor 15, at least one force sensor 48, at least one EMG sensor 14, at least one neuromuscular electrical stimulation (NEMS) device 22 for providing low-level neuromuscular stimulation. The real-time clock/calendar 52 is powered by a battery mounted on the printed circuit board when the power is off. The clock 52 maintains the time and date continuously. Records of patient use, active range of motion, extensor resistive torque, and EMG activity are recorded with a time stamp in a non-volatile serial EEPROM memory device 50. Data is kept safe, even when no power is applied to the memory 50. These records can be downloaded to a therapist's or patient's personal computer. A patient record can be printed that provides a performance history and compliance by date. A display 20 is made available for viewing and monitoring joint/muscle activity during therapy.

The microprocessor 44 controls the activation of the air muscle by operating the microcompressor and/or the air valves. Wrist/joint position may be displayed as a bar graph or as numbers on the LCD display 20. The degree of flexor resistance torque measured by the at least one force sensor, and/or electrical activity from the EMG sensor may be displayed as a variable length line of lit light emitting diodes (LEDs) incorporated next to the LCD display 20. The changing goal for active wrist motion may be displayed as a line on the LCD graph. One line of multi-color light emitting diodes (LEDs) may indicate the degree of flexor resistance torque as measured by the force sensitive resistors. A second line of LEDs may indicate the EMG activity of the wrist or finger extensors. The microcompressor, air valves, microprocessor, and the LCD may be portably located on or beside the patient during therapy sessions. Alternatively, feedback may be provided to the patient/therapist through audio signals (e.g., by varying the tonal frequencies, amplitudes, etc.). Records of patient use, active range of motion, extensor resistive torque, and EMG activity are recorded with a time stamp in an electronic memory device (e.g., a non-volatile serial EEPROM). The electronic memory system can provide stored information, such as patient compliance and patient performance, from the electronic memory to a therapist/patient on command. Thus, the system includes a mechanism for the patient to monitor the compliance and performance through visual and possibly aural means. Moreover, the controller may update the displays in a predetermined manner to provide a mechanism for the patient to improve performance and compliance for neuromuscular function reeducation and for restoring physical function of the neuromuscular system in the patient.

The present invention provides neuromuscular reeducation and restoration of physical function of the neuromuscular system in the patient through (1) biofeedback, (2) repetitive task practice, and (3) neuromuscular electrical stimulation (NMES). Furthermore, psychological research has shown that an important part of biofeedback stimulated neuromuscular reeducation is shaping, which is defined by psychologists as establishing goals just beyond current capability and changing goals as progress is made. The present invention also provides shaping through measurements obtained during therapy session. Additionally, research has shown that many repetitions are necessary for permanent neuromuscular reeducation. To encourage practice of the repetitions, the present invention records compliance of a patient with the repetitive therapy and provides a report back to the patient's therapist.

One method for implementing a protocol, for the system as described, for restoring physical function of the neuromuscular system comprises measuring a signal indicative of the activity of the muscle through the EMG sensor(s) 14; measuring a signal indicative of the joint motion through a joint position sensor 15, where the joint is associated with the neuromuscular system; measuring another signal indicative of the muscle resistance through the force sensor 48; mapping the measured signals to at least one parameter; and controlling the air level in the air-muscle 10 in order to optimize the parameter for restoring physical function of the neuromuscular system associated with the joint in the patient.

Figure 6:
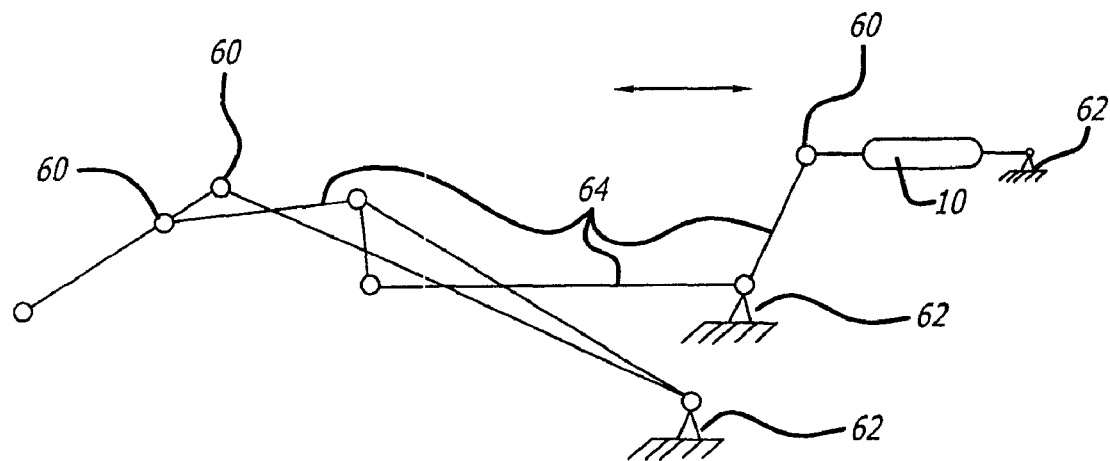
FIG. 6 shows the pivot points and trajectory taken by the motion causing device, such as an air-muscle, according to one aspect of the present invention.
Figure 7:
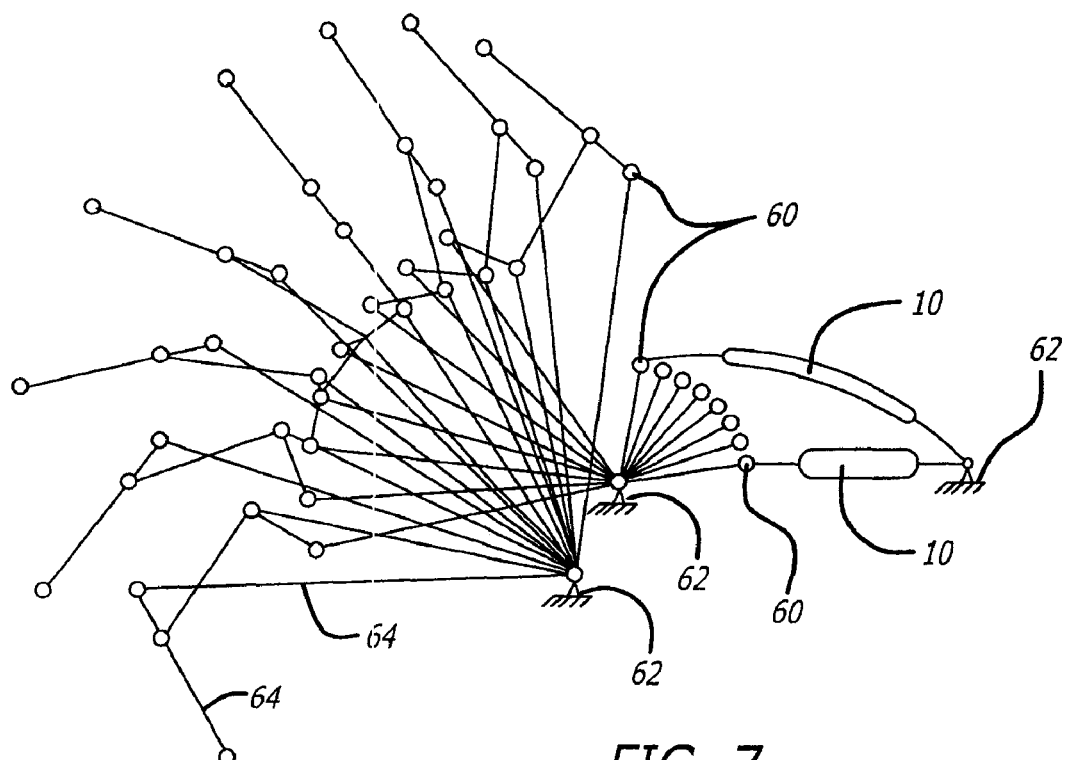
FIG. 7 shows the pivot points and trajectory taken by the motion causing device, such as an air-muscle, according to another aspect of the present invention.

FIGS. 6 and 7 depict one arrangement of pivot points 60 and linkages 64 associated with the air-muscle 10 attached to forearm supports (as depicted by 62). The air-muscle 10, upon inflation and deflation, permits the arm and joints to achieve pre-determined trajectories (shown as spiral type in the figures). Hence, the pivot point 60 positions and the trajectories of the arm (or linkages 64) can be controlled by inflating/deflating the air-muscle 10 in a manner to get optimal motion for the arm and joint thereby providing means for effective restoration of the physical function of the neuromuscular system. For example, in FIG. 6, the air muscle 10 is shown connected at one end to the forearm support 62 while at the other end it is depicted as being attached to pivot point or driving point 60. When the air-muscle 10 is inflated/deflated in a specific manner optimal motion is achieved for reeducation and restoration of the neuromuscular system.

Figure 10:
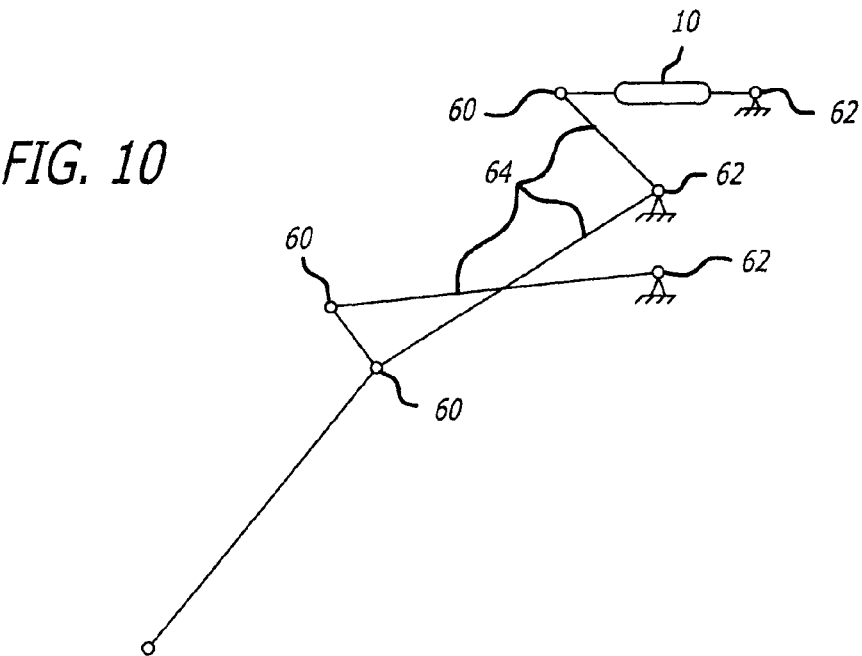
FIG. 10 is an alternative embodiment, with reduced linkages, showing the pivot points and trajectory taken by the air-muscle.
Figure 11:
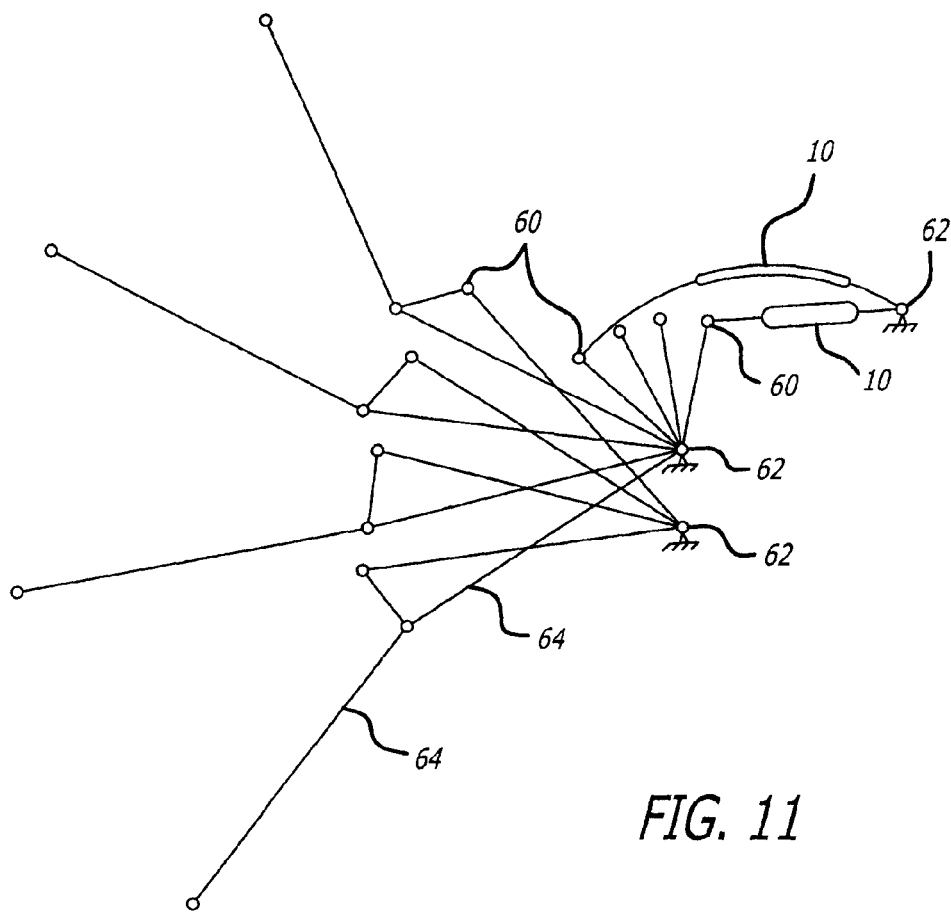
FIG. 11 is yet another embodiment, with reduced linkages, showing the pivot points and trajectory taken by the air-muscle.

In an alternative embodiment, as depicted in FIGS. 10, 11, there is a reduction in the number of linkages (over the embodiment of FIGS. 6 and 7) but the muscle is still able to achieve the same trajectory and motion.

Figure 8:
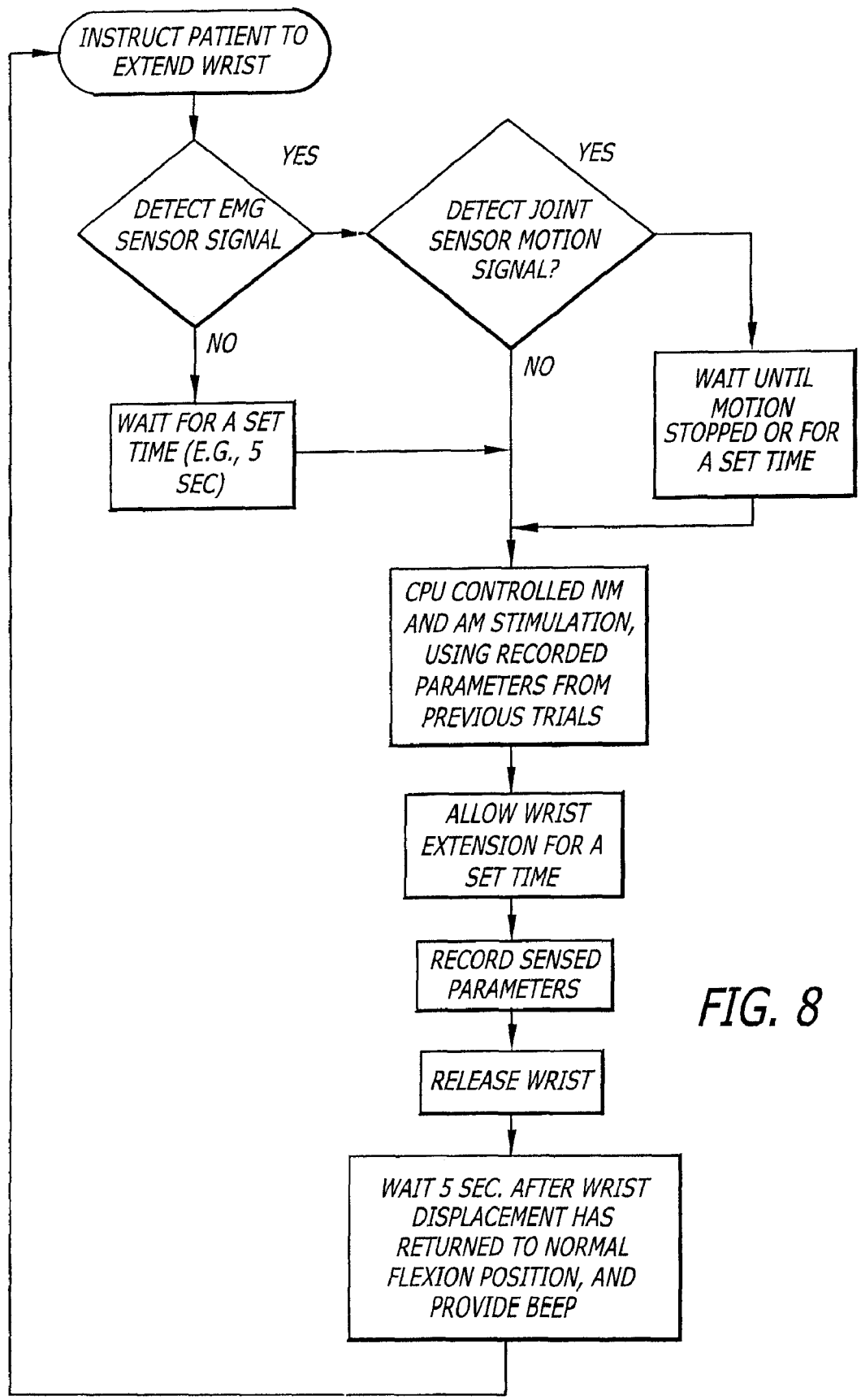
FIG. 8 is a flow chart depicting one embodiment for the protocol for neuromuscular function reeducation and restoring physical function of at least one neuromuscular system.

FIG. 8 is a flow chart depicting another embodiment of the protocol for restoring physical function of the neuromuscular system. Specifically, the patient is instructed to try to extend the wrist when a beep is heard. The EMG activity of the wrist extensors and the motion of the wrist are recorded in the memory of the device and displayed for the patient. The patient could be instructed to use the device for 6 hours a day, although more usage may be allowed, and the treatments need not be continuous. The patient could start and stop the device at any time. The first 2 hours could focus on EMG and joint position feedback. During the second 2 hours the flexor resistance torque from the flexors could be used as the feedback signal to help the patient reduce any flexor spasticity. The final 2 hours of therapy would include both extensor EMG and flexor resistance torque as feedback. The number of completed cycles could be recorded for each day as well as the time for each cycle and the total treatment time for each day. The patient could be encouraged to grasp a block and lift it several times during a day and at the end of each therapy session. After grasping, the patient may be encouraged to try and lift and subsequently move the block. The patient may also be encouraged to keep a record of successful attempts.

In the protocol, the level of extensor EMG activity may be indicated by LEDs on the display 20. A level equal to that obtained at the last clinic therapy session would show as a yellow light. A level below would generate a buzzing sound. A green LED would indicate a higher level. Faster flashing LEDs indicate higher levels of EMG activity. The output of the joint position sensor is displayed on the LCD by a bar. If motion exceeds this line a pleasant sound is heard. After every day, the line that represents the goal could be increased/updated by a certain amount (e.g., 1% of the highest joint motion achieved in the previous day). Thus, joint position could serve as the basis for subsequent training each day.

During training, whenever motion has stopped for a certain period (e.g., 3 seconds), the air-muscle could be activated and the wrist and finger extension may be completed. The extension could be held for a certain amount of time (e.g., 3 seconds) and then released. The torque of the flexor resistance is measured and displayed on flashing red LEDs during the process (the higher the force, the faster the blinking). The patient could be instructed to try to minimize this force by thinking about relaxing the flexors. A system delay (for e.g., of about 10 seconds) may be introduced and the process would be started over with an auditory beep.

The number of hours of operation of the device and the active motion achieved at the beginning of a day and at the end of each day may be recorded in memory. This information would provide fairly accurate information about patient compliance and permits matching of timed data from patient reports of self-documentation of training. When the device is turned on for the first time each day, these parameters are displayed for the patient on the LCD.

The memory may be downloaded onto a PC in the clinic. A summary chart graphically displaying the number of hours of use a day by the patient, the range of motion change per day and the change of active range of motion day to day may be displayed and the charts printed for the patient file.

In another aspect for providing therapy to a patient, the therapist can prescribe the patient as to how much time he or she can spend on a specific program. In essence, the amount of emphasis on each program depends on the symptoms of the patient. For example, the program could require work on the extensor muscle recruitment. To this end, the extensor EMG signal may be displayed as a line of LED lights on a relative scale. Alternatively, a single color-coded or intensity coded LED could be used. The range between the minimum and maximum signal measured may be about 60% of the height of the LED line. Messages may be provided on the LCD display 20 to encourage the patient to increase the display level.

A second program, that could be selected by the patient, includes measurement of the resistance offered by the flexor muscles (antagonist resisting muscles) to an extension process. It is common for patients with neuromuscular diseases to develop a constant muscle contraction. Specifically, the flexors are substantially stronger than the extensors which causes the characteristic flexed fingers and wrist that can be seen in many patients. The reason for this is the lack of inhibition present in the central nervous system. To retrain the neuromuscular system, the program could display the relative magnitude of the measured resistance and request the patient to consciously try and reduce the signal on the display. EMG sensors 14 located adjacent the flexor muscles and/or FSRs 48 or lack of full extension may be used for measuring the resistance. The program may also require the patient to extend the wrist with the air muscle to about neutral position. At this point EMG activity or the force output of the FSRs may be measured for the flexor muscles (antagonist resisting muscles). Subsequent calculation of the active stiffness generated by the flexors may be achieved by dividing the measured force by the amount of joint displacement (as measured by the potentiometer 15).

A third program that can be selected for the patient permits (i) increasing the activity of the extensors, and (ii) simultaneously decreasing the activity of the flexors. The signal to one of the LED lines may be a combination of the magnitude of the extensor signal, and the flexor signal as measured either via the EMG sensor 14 or the FSR 48. The patient may be asked to extend their fingers and wrist and then to think about their forearm so as to minimize the signal displayed via the LED lines.

It is well established that continuous passive motion entails inducing movement of certain limbs/joints without requiring muscle co-ordination, strength, or control by a patient. Numerous studies have shown that CPM of the different limbs and joints accelerates healing, and importantly results in a fuller range of motion of the joint at the end of the course of the therapy.

Figure 9:
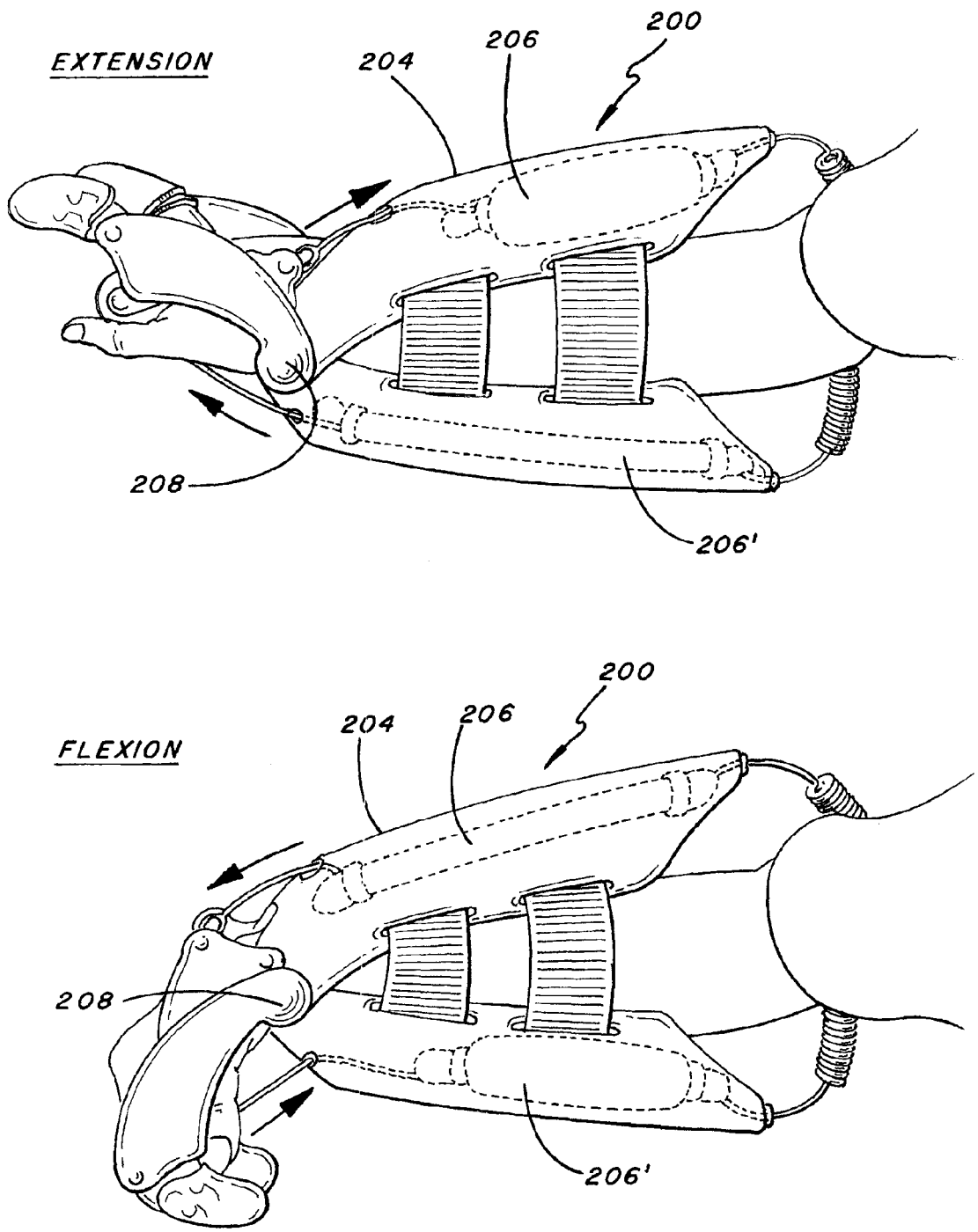
FIG. 9 is one embodiment of the invention using a continuous passive motion (CPM) device in conjunction with an air-muscle device.

Thus, in another aspect of the system 200, as shown in FIG. 9, a continuous passive motion (CPM) device 204, in conjunction with an air-muscle device 206 and 206', may be used for providing flexion and extension to the joint 208 of the patient for reeducation and restoration of the physical functions of the neuromuscular system in a patient. During extension, the upper air-muscle device 206 may be controllably activated, whereas during flexion, the lower air-muscle device 206' may be controllably activated. By providing a controlled activation of the air-muscle device in the CPM, it is possible to provide reeducation and restoration of the neuromuscular system.

In another embodiment of the present invention the air-muscle is modified so that it is capable of interacting with a personal computer based virtual reality program for capturing the interest of the user. The resulting system allows extension of the existing wrist/hand device through coordinated elbow and shoulder motions.

A prerequisite for the elaborate movements of the upper extremity, lower extremity gait, and dexterous abilities of humans in general is the ability to coordinate multiple joints and regulate forces produced by limb segments. Research data indicate that patients with stroke exhibit deficits in the ability to precisely control forces produced. However, with the air-muscle device, the inventors have found that this therapy improves patients' ability to control grasping forces during a general force-tracking task and a functional task (e.g. turning a key in a lock).

While the disturbance of voluntary upper extremity movement in patients with stroke is typically apparent upon visual examination, little is known about the mechanisms responsible for these disturbances due in part to the dearth of quantitative studies of multi-joint movements in such patients. During a target-directed pointing task, patients with stroke could reach into all parts of the workspace with their affected limb, suggesting that movement planning was intact for these patients. However, when inter-joint coordination was assessed by expressing elbow angle as a function of shoulder angle, patients with stroke exhibited an irregular and variable relationship. This disruption in inter-joint coordination resulted in movement paths that were more segmented and variable. It has been shown that prehension (reaching and grasping) movements of patients with stroke were characterized by a spatiotemporal dyscoordination between the arm and trunk. As a result, patients developed a new pattern of coordination represented by more trunk recruitment during prehensile actions. More recently, a kinematic analysis of reaching movements of patients with stroke indicated that patients with stroke, unlike healthy controls, recruited the trunk to assist in transporting the hand to the object. Thus, these patients were recruiting a new degree of freedom (e.g. the trunk) to perform this task. Further kinematic studies have shown that patients with stroke have a more variable: reaching path, orientation of the hand relative to the object, final hand position on the object, and a disruption in inter-joint coordination. These data suggest that patients with stroke have difficulty with motor execution. Therefore rehabilitation of the affected upper extremity with the air-muscle is oriented toward restoring the normal sensorimotor relationships between the joints.

A consistent factor in laboratory and clinical studies of neuroplasticity is that to obtain reorganization of the neural system, cognitive input must be present and many repetitions are required. Also, studies have shown that concentrating on the effects of their movement rather than specific body movements enhances the effect. In other studies, there is some evidence that training in only one or two coordinated movements transfers to improvements in other tasks.

Therefore for the upper extremity, the therapeutic protocol chosen, for exemplary purposes according to one aspect of the invention, is to focus on two important tasks; reaching and eating. Specifically, the patient is requested to achieve either a reaching task or an eating task. After the patient has achieved his/her maximal motion, the device assists the limb to complete the task. Feedback of self-actuated progress is recorded and fed back to the patient.

In summary, a critical review of rehabilitation approaches to reduce impairments and improve upper extremity mobility among patients following stroke would lead to the conclusion that repetitive task practice incorporating biofeedback strategies can improve functional and mobility of patients with chronic stroke. When one adds to the growing limitations on treatment time, it seems reasonable to speculate that treatments emphasizing repetition of functionally related tasks, performed in the home environment could enhance function and improve health related quality of life. This earlier relocation for centralization of stroke therapy into the home appears effective in promoting motor and functional gains while yielding substantial patient satisfaction. Complementing this approach through inclusion of devices that reinforce the need for volitional activation of joint movement while concurrently offering knowledge of results about range of motion, muscle activity or resistance to movement could be beneficial if such devices were reliable, easy to use, cost-effective, and conducive to home and clinical use.

Figure 12:
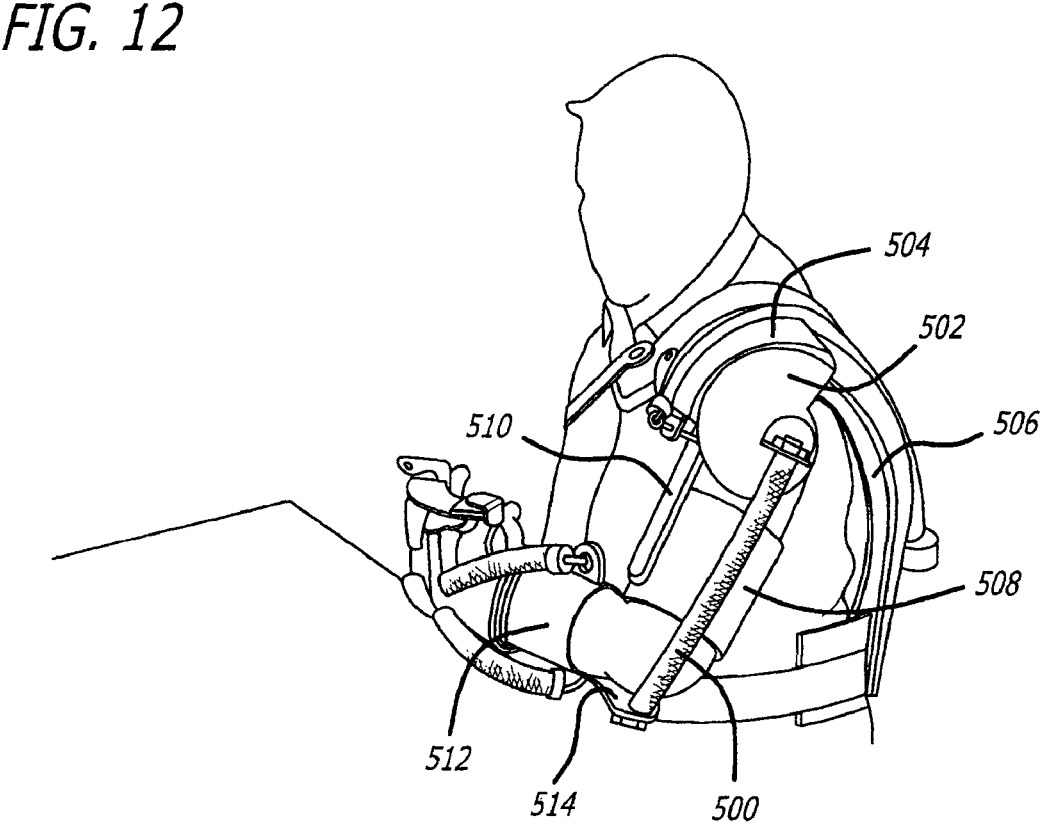
FIG. 12 is an initial state of the air-muscle device used in conjunction with a robotic system for providing assistive training.
Figure 13:
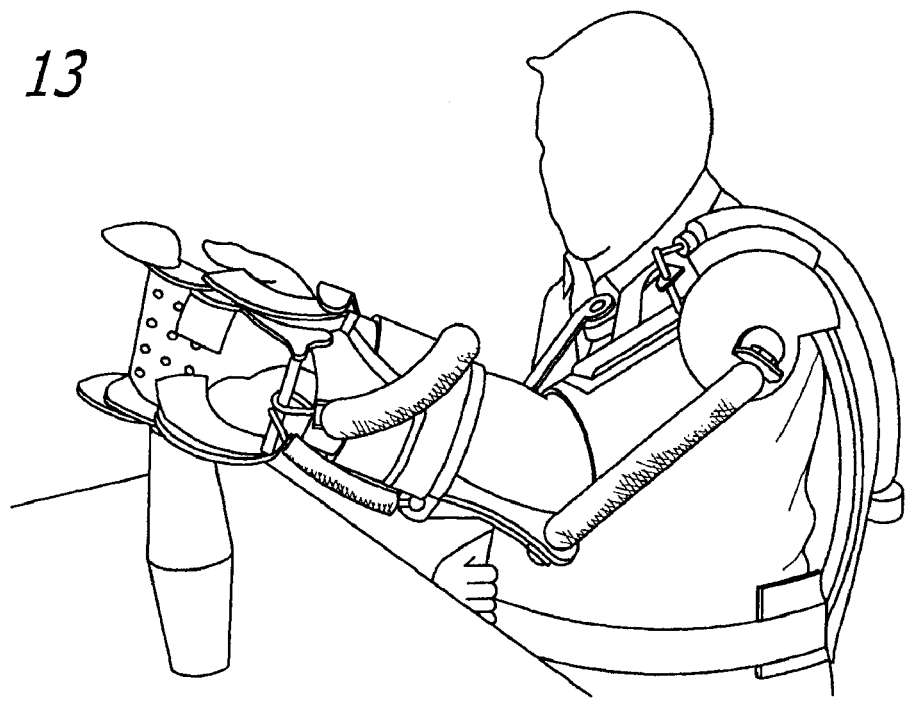
FIG. 13 is an intermediate state of the air-muscle device used in conjunction with a robotic system for providing assistive training.

FIGS. 12-14 show various states of the air-muscle device used in conjunction with a robotic system for providing assistive training. The design philosophy is such that it encourages volitional activation of joint movement through feedback range of motion, muscle activity and resistance to movement and then completing the task for the patient. In one aspect, for exemplary purposes, the system is adapted to provide training of two tasks (viz., feeding and reaching). It is anticipated that training of coordinated joint movement for these two tasks will lead to more general improvement in related functional tasks as found in other feedback therapies.

To train for the reaching motion, the robot system abducts the shoulder in the flex direction, extends the elbow, supinates the forearm, and extends the wrist and fingers. Training begins with the patient facing a table with her/his forearm resting on the table transverse to the torso (in a plane parallel to the frontal plane) as shown in FIG. 12. In one aspect of the invention, the shoulder motion is restricted to flexion in the sagittal plane. Thus, the intermediate reaching position is shown in FIG. 13.

To train for an eating motion, the robotic system flexes the shoulder, supinates the forearm, and extends the wrist as shown in FIG. 14. Most stroke patients have the ability to flex their elbow, so this function may be left to the patient. The assisted movements may be made in a slow manner to protect against significant increases in muscle tone.

Thus, as shown in the FIGS. 12-14, the air muscle 500 rotates the shoulder in abduction and flexion. A plastic hinge 502 only allows motion in the sagittal plane. The normal internal rotation of the humerus is held in neutral by the distal and proximal strapping system. The proximal air muscle rides on a plate 504 that rotates about the center of rotation of the humerus. A foam-lined sub-plate 506, which is attached to the torso with Velcro straps, distributes the vertical reaction of the air muscle. A plastic cuff 508 is attached to the upper humerus with Velcro straps. This serves as an attachment point for a driver 510 that is connected at its other end to the sliding plate that rests on top of the sub-plate. Contraction of the air muscle rotates the upper plate 504 in an arc about the center of rotation of the humerus. A potentiometer (not shown) centered on the axis of rotation records the amount of shoulder motion.

To control elbow motion, a hinge (not shown) is attached at the elbow with straps to the distal humerus and proximal forearm. A potentiometer is contained in the center of rotation of the hinge to measure elbow flexion and extension. The forearm piece 512 has an extension 514 that is used an attachment point for an air muscle. The proximal end of this air muscle is attached to the center of rotation of the humerus.

Supination/pronation, plus coordinated extension of the wrist and fingers is obtained by a modification of the wrist/hand device that has been clinically tested and currently is in commercial distribution. Two muscles are attached to the hand/wrist device. The proximal end of one is attached to the inside of the forearm at the elbow and the other proximal end of the other one is attached to the outside of the forearm at the elbow. If the latter muscle is contracted, combined wrist and finger extension occurs along with supination of the forearm. If the other muscles contracts, combined wrist and finger extension occurs along with pronation of the forearm. A potentiometer is located at the center of rotation of the wrist. Initially, no measurement of pronation/supination will be included.

The above described system and programs thus provide effective and easy to use functionality for reeducation and restoration of the physical functions of the neuromuscular system in a patient. The system is inexpensive, portable, comfortable, and easy to use either by the patient or by a therapist.

In summary, the system and method according to the present invention is a self-contained, mobile device, implementing a protocol, and which provides visual and/or aural feedback of wrist and finger position, measurement of extensor and flexor activity for neuromuscular function reeducation and restoring physical function of at least one neuromuscular system in a patient.

The attached description of exemplary and anticipated embodiments of the invention has been presented for the purposes of illustration and description. They are not intended to be exhaustive or to limit the invention to the precise forms disclosed. Many modifications and variations are possible in light of the teachings herein. For example, a suitable inflatable device or mechanical drive can be used in replacement for the air-muscle. Additional sensors could be used for measuring critical parameters for restoring physical function. Multiple motion causing devices could be simultaneously connected at various positions on the patient's body, and the devices could be controlled by multiple or single controllers. Also, there could be a single display configured to provide feedback on several different measured parameters. The therapist could be allowed to select, from a menu provided through the display, unique therapeutic protocol(s) for a specific patient. Furthermore, the frequency of patient use and the ability to reach performance goals can be recorded in memory and the record played back for the therapist/patient. While the specification describes particular embodiments of the present invention, those of ordinary skill can devise variations of the present invention without departing from the inventive concept.

We claim:

1. A method implementing a protocol for restoring physical function of at least one neuromuscular system associated with a joint in a patient, the method comprising:
   measuring a first signal indicative of the activity of said muscle through an EMG sensor;
   measuring a second signal indicative of the joint motion through a joint position sensor;
   measuring a third signal indicative of the muscle resistance through a force sensor;
   mapping the measured signals to at least one parameter; and
   controlling the air level in an inflatable device in order to optimize said parameter for restoring physical function of said muscle associated with the joint in the patient, the inflatable device being adjacent to the joint and being inflated or deflated through at least one port associated with the device.

2. The method according to claim 1, further including storing information in an electronic memory system, said information including patient compliance and patient performance.

3. The method according to claim 2 wherein the electronic memory system is located remotely from the patient.

4. The method according to claim 1 including providing a computer processor for implementing the protocol.

5. The method according to claim 4 wherein the computer processor is located remotely from the patient.

6. The method according to claim 2, further including providing the stored information from the electronic memory system to the therapist and/or patient on demand.

7. The method according to claim 1, wherein the EMG sensor is used for measuring the electrical activity of an agonist resisting neuromuscular system.

8. The method according to claim 1, wherein the force sensor is used for measuring the force signal from an antagonist resisting neuromuscular system.

9. The method according to claim 1, wherein the force sensor is a force sensitive resistor.

10. The system according to claim 1, wherein the force sensor is the pneumatic muscle wherein the force is obtained from displacement and pressure measurements of the pneumatic muscle.

11. The method according to claim 2, further including the step of displaying the electrical activity from the EMG sensor to the patient through a first display.

12. The method according to claim 11, further including the step of displaying a degree of flexor resistance torque measured by the force sensor through a second display.

13. The method according to claim 12, wherein the displays provide a means for the patient to monitor the compliance and performance.

14. The method according to claim 13, further including the step of updating the displays to provide a mechanism for the patient to improve said performance and said compliance.

15. The method according to claim 1, further providing stimulation through at least one neuromuscular stimulating electrode to the neuromuscular system.

16. A method implementing a protocol for restoring physical function of at least one neuromuscular system associated with a joint in a patient, the method comprising:
   providing at least one joint position sensor for detecting self-actuation of a joint and measuring a joint motion;
   providing a computer processor for implementing a protocol responsive when self-actuation is detected by the at least one joint position sensor but the measured joint motion has not achieved a predetermined value or when self-actuation is attempted but the measured joint motion has not achieved a predetermined value;
   providing electronic memory for storing the protocol; and
   providing a motion causing device for assisting the at least one joint in movement, said motion causing device following the protocol implemented by the computer processor such that the joint motion achieves the predetermined value.

17. The method according to claim 16, wherein the motion-causing device is an air-muscle.

18. The method according to claim 16 wherein the computer processor is located remotely from the patient.

19. The method according to claim 16 wherein the electronic memory system is located remotely from the patient.

* * * * *